United States Patent [19] [11] 4,276,411
DiGiacomo et al. [45] Jun. 30, 1981

[54] LAYERED ORGANOPHOSPHORUS INORGANIC POLYMERS CONTAINING ACYCLIC GROUPS

[75] Inventors: Peter M. DiGiacomo, Mission Viejo; Martin B. Dines, Santa Ana, both of Calif.

[73] Assignee: Occidental Research Corporation, Irvine, Calif.

[21] Appl. No.: 60,079

[22] Filed: Jul. 24, 1979

[51] Int. Cl.³ .................. C08G 79/04; C08G 79/00
[52] U.S. Cl. .................. 528/395; 260/429.1; 260/429.2; 260/429.3; 260/429.5; 260/435 R; 528/398
[58] Field of Search .................. 528/395, 9

[56] References Cited

U.S. PATENT DOCUMENTS 3,654,189   4/1972   Venezky .................. 260/31.2 R
3,663,460   5/1972   Block et al. .................. 528/9

Primary Examiner—Wilbert J. Briggs, Sr.
Attorney, Agent, or Firm—Christie, Parker & Hale

[57] ABSTRACT

Solid inorganic polymers which are derivatives of acyclic organo group-containing phosphonic or phosphoric acids are characterized by the structural linkage of three oxygens bonded to phosphorus to one or more tetravalent metals selected from the group consisting of titanium, zirconium, cerium, hafnium, lead, thorium and uranium. The molar ratio of phosphorus to tetravalent metal is about 2 to 1. One use for the polymers is as stationary phases or supports in chromatography.

25 Claims, 8 Drawing Figures

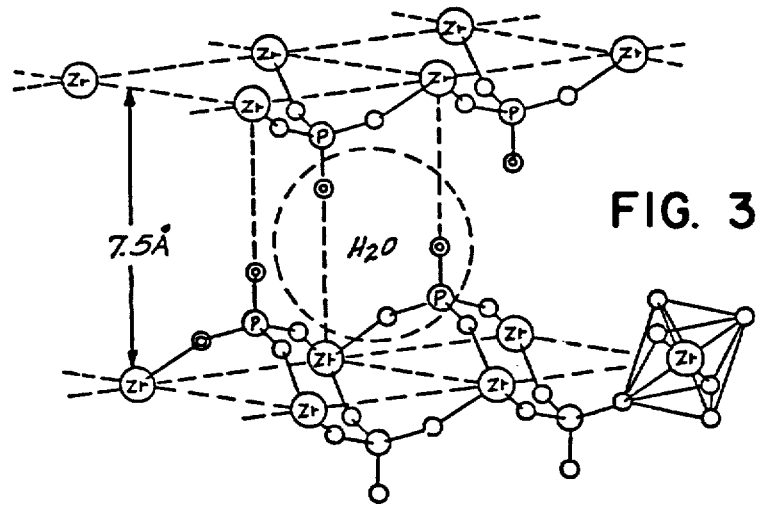
FIG. 3
FIG. 5
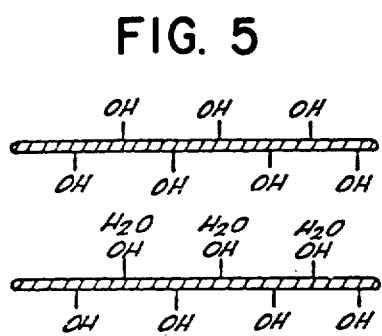
FIG. 4
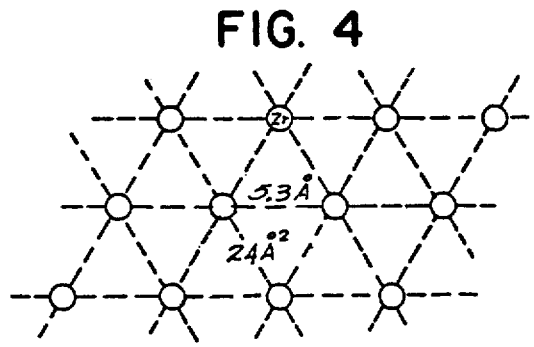
FIG. 6
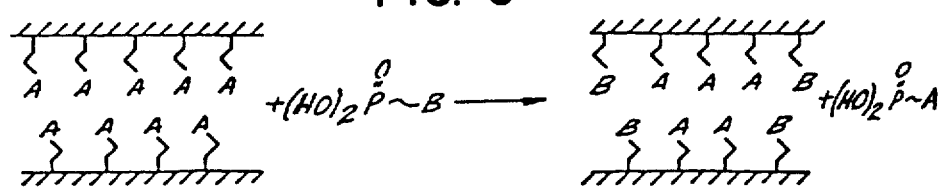

LAYERED ORGANOPHOSPHORUS INORGANIC POLYMERS CONTAINING ACYCLIC GROUPS

CROSS-REFERENCE TO RELATED APPLICATIONS

This application is related to the following copending applications: Ser. No. 945,971 filed Sept. 26, 1978, now U.S. Pat. No. 4,232,146 issued Nov. 4, 1980, Ser. No. 952,228 filed Oct. 17, 1978, now U.S. Pat. No. 4,235,990 issued Nov. 25, 1980, Ser. No. 966,197 filed Dec. 4, 1978, now U.S. Pat. No. 4,235,991 issued Nov. 25, 1980, Ser. No. 7,275 filed Jan. 29, 1979, Ser. No. 43,810 filed May 30, 1979 and titled Process for Preparing Layered Organophosphorus Inorganic Polymers, Ser. Nos. 54,107 and 54,097 filed July 2, 1979 and titled, respectively, Layered Cyano End Terminated Organophosphorus Inorganic Polymers and Layered Organophosphorus Inorganic Polymers Containing Mercapto or Thio Groups, and four applications filed concurrently herewith, and titled: Layered Organophosphorus Inorganic Polymers Containing Cyclic Groups, Ser. No. 60,077 Layered Organoarsenous Inorganic Polymers, Ser. No. 60,078 Layered Organophosphorus Inorganic Polymers Containing Mixed Functional Groups, Ser. No. 60,250 and Layered Organophosphorus Inorganic Polymers Containing Oxygen Bonded to Carbon Ser. No. 60,249. The entire disclosure of each of these applications is hereby incorporated herein by this reference.

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids are responsive regions of chemical and physical action. In many practical chemical and physical phenomena such as absorption, corrosion, inhibition, heterogeneous catalysis, lubrication, ion exchange activity, adhesion and wetting and electrochemistry, activity occurs as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in their active sites which arises from the nature of their surface structure. Furthermore, much of the active sites are usually buried within the surface, and as a result of these two factors, elevated temperature and low conversions are typically encountered. Exceptions in which homogeneous catalysts are employed have been the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Efforts at heterogenizing catalysts have been discussed by Bailar, "Heterogenizing Homogeneous Catalysts," Catalysis Reviews—Sci. & Eng. 10(1) 17–35 (1974) and Hartley and Vezey, "Supported Transition Metal Complexes as Catalysts," Advances in Organometallic Chemistry 15, 189–235(1977). The entire disclosure of which is incorporated herein.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "interclalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, this potential surface will be greater than the actual surface by a factor of the number of lamella composing the crystal. This value is typically on the order of $10^2$–$10^4$. Although edge surface is practically insignificant compared to basal surface, it is critical in the rate of intercalation, since the inclusion process always occurs via the edges. This is because bonding within the sheets is strong, and therefore, basal penetration of the sheets is an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process on deintercalation the guests undergo only minor perturbation.

In order for a more active process to occur during intercalation, such as selective complexation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ion or van der Waals forces of intercalated guests were operating.

One of the few layered compounds which have potential available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be promising inorganic cation exchanger for alkali, ammonium and actinide ions, Alberti, "Accounts of Chem. Research", 11, 163 (1978), incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. S. Yamaka described the reaction of this solid with ethylene oxide, which does not simply incorporate between the layers as do the other organics, but rather was found to irreversibly react with the acidic hydroxyls to form a covalently bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound inorganic alkanol groups. This conversion, while of interest, has limited if any improvement over the hydroxyls already available on zirconium phosphate.

A very recently reported effort in the field is Alberti, et al., "J. Inorg. Nucl. Chem.", 40, 1113 (1978) which is incorporated herein by reference. A method similar to that of this invention for the preparation of zirconium bis(benzenephosphonate), zirconium bis(hydroxymethanephosphonate) monohydrate, and zirconium bis(monoethylphosphate) is described, with descriptions of the properties for these products.

Following the Alberti publication, a paper by Maya appeared in "Inorg. Nucl. Chem. Letters", 15, 207 (1979), describing the preparation, properties and utility as solid phases in reversed phase liquid chromatography for the compounds $Zr(O_3POC_4H_9)_2.H_2O$, $Zr(O_3POC_{12}H_{25})_2$ and $Zr(O_3POC_{14}H_{21})_2$. All of the compositions that are described herein can be useful in gas phase, liquid phase, gas liquid, reversed phase, and bulk and thin layer chromatography. The compounds can also be useful as hosts and carriers for organic molecules and especially biologically active organic molecules (e.g. methoprene).

SUMMARY OF THE INVENTION

According to the present invention there is provided solid inorganic polymers having organo groups covalently bonded to phosphorus atoms and in which the phosphorus atoms are, in turn, covalently bonded by oxygen linkage to tetravalent metal atoms and, when formed in a layered crystalline state, provide the organo groups on all of the apparent and interlamellar surfaces.

More particularly, the invention relates to layered organophosphorus inorganic polymers containing acyclic organo groups. The process of preparation comprises a liquid medium reaction in which at least one organophosphorus acid compound of the formula:

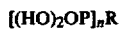

$$[(HO)_2OP]_nR$$

wherein n is 1 or 2 and R is an organo group covalently coupled to the phosphorus atom, and wherein when n is 2, R contains at least two carbon atoms and is directly or indirectly coupled to phosphorus atoms through different carbon atoms whereby the two phosphorus atoms are separated by at least two carbon atoms, is reacted with at least one tetravalent metal ion preferably selected from the group consisting of zirconium, cerium, thorium, uranium, lead, hafnium and titanium. The molar ratio of phosphorus to the tetravalent metal is 2 to 1. Reaction preferably occurs in the presence of an excess of the organophosphorus acid compound and the metal ion is provided as a compound soluble in the liquid medium.

Where only one specie of an organophosphorus acid compound is provided as the reactant with the tetravalent metal compound, the end product will have the empirical formula $M(O_3PR)_2$. Phosphoric and/or phosphorous acid can also be present as reactive dilutants to form part of the solid inorganic polymeric structure which is the product of the reaction.

The products formed are layered crystalline to amorphous in nature. For all products, the R groups may be directly useful or serve as intermediates for the addition or substitution of other functional groups. When the product is crystalline and n is 2, cross-linking between the interlamellar layers occurs.

The normal liquid medium is water. However, organic solvents, particularly ethanol, may be employed where water will interfere with the desired reaction. Preferably, the solvent is the solvent in which the organophosphorus acid compound is prepared. Where the organophosphorus acid compound has a sufficiently low melting point, it can serve as the liquid media.

The metathesis reaction occurs at temperatures up to the boiling point of the liquid medium at the pressures involved, typically from ambient to about 150° C. more preferably from ambient to about 100° C. While formation of the solid inorganic polymer is almost instantaneous, the degree of crystallinity of the product can be increased by refluxing the reaction products for times from about 5 to 15 hours. Crystallinity is also improved by employing a sequestering agent for the tetravalent metal ion.

THE DRAWINGS

Figure 1:
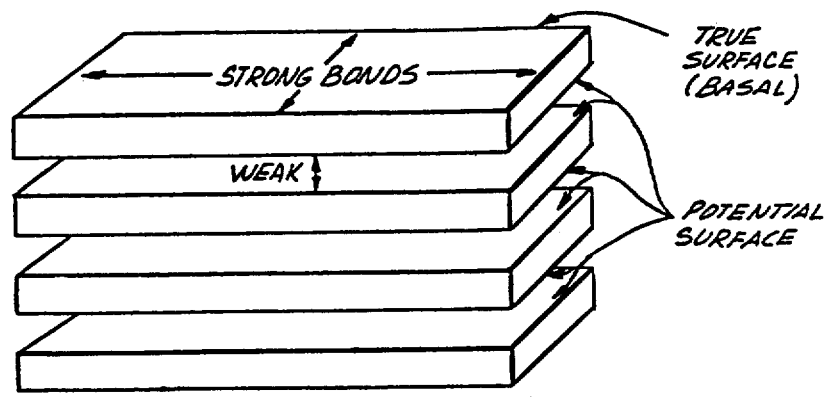
FIG. 1 illustrates a layered microcrystal. Each lamellar slab is formed of strong covalent bonds and has a thickness of about 10 atoms.
Figure 2:
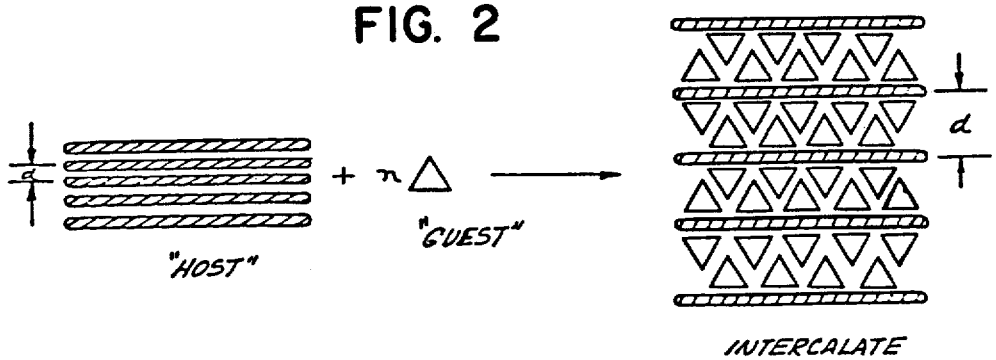
FIG. 2 illustrates intercalation where the interlayer distance is shown as "d."

FIG. 3 illustrates the accepted structure for zirconium phosphate and spacing between layers. The dashed lines between zirconium (Zr) atoms is to establish the plane between them. In the drawing P=phosphorus, O=oxygen and water of hydration is shown.

FIG. 4 illustrates a projection of zirconium plane showing accepted spacing between Zr atoms and the available linkage area.

FIG. 5 is a symbolized depiction of spaced zirconium phosphate layers showing covalently bonded hydroxyl groups and water of hydration.

FIG. 6 illustrates an exchange reaction between anchored groups "A" and groups to be substituted for "B", and ν represents the portion of the organo group linking the terminal group "A" or "B" to the crystals or the organophosphorus acid compound reactant.

Figure 7:
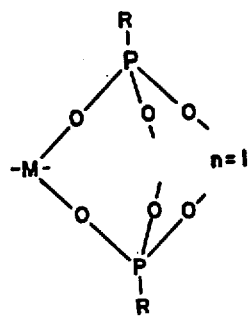

FIG. 7 shows the basic structural unit of the inorganic polymer formed by the process of the invention where n is 1 and where P=phosphorus atom, O=oxygen atom, M=tetravalent metal atom and R is the organo group.

Figure 8:
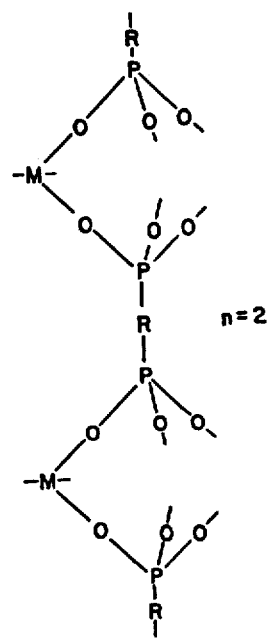

FIG. 8 shows the basic structural unit of the inorganic polymer formed by the process of the invention where n is 2 and where P=phosphorus atom, O=oxygen atom, M=tetravalent metal atom and R is the organo group.

DETAILED DESCRIPTION

According to the present invention there is provided solid inorganic polymers in layered crystalline to amorphous state by the liquid phase metathesis reaction of at least one organophosphorus acid compound having the formula:

$$[(HO)_2OP]_nR$$

wherein n is 1 or 2 and R is an acyclic organo group covalently coupled to the phosphorus atom, with at least one tetravalent metal ion selected from the group consisting of zirconium, thorium, cerium, uranium, lead, hafnium and titanium to form a solid inorganic polymer precipitate in which phosphorus is linked to the metal by oxygen and the organo group is covalently bonded to the phosphorus atom. Where, in the organophosphorus compound, n is 2, the end product occurs in the bis configuration. In this configuration, R must contain two or more carbon atoms, preferably from two to about twenty carbon atoms, such that at least two carbon atoms separate the phosphorus atoms. In this bis configuration no single carbon atom is bound directly or indirectly to more than one [PO(OH)$_2$] group. When n is 1, and as depicted in FIG. 7, the organo groups will be pendant from phosphorus atoms. When n is 2, and as depicted in FIG. 8, cross-linking will occur between interlamellar surfaces of the crystalline end product. Typically, the tetravalent metal ion is provided as a soluble salt MX wherein M is as defined above and X is the anion(s) of the salt. The typical anions include halides, $HSO_4^{-1}$, $SO_4^{-2}$, $O_2C-CH_3^{-1}$, $NO_3^{-1}$, $O^{-2}$ and the like.

The majority of the polymeric reaction products formed are found to be layered crystalline or semi-crystalline in nature and, as such, provided layered structures similar to zirconium phosphates. The remainder are amorphous polymers possessing a large quantity of available pendant groups similar to silica gel.

By the term "organophosphorus acid compound", as used herein, there is meant a compound of the formula:

$$[(HO)_2OP]_nR$$

wherein n is 1 or 2, R is any group which will replace a hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is presently preferred.

When, in the organophosphorus compound, n is 2, the end product occurs in the bis configuration. In this configuration, R must contain two or more carbon atoms, preferably from two to about twenty-six carbon atoms, such that at least two carbon atoms separate the phosphorus atoms. In this bis configuration, no single carbon atom is bound directly or indirectly to more than one [PO(OH)$_2$] group. Thus the groups which link to the metal have the basic structural formula:

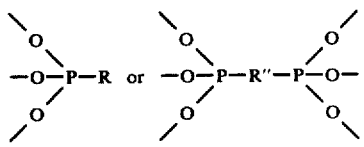

wherein R" is a bis group containing at least two carbon atoms bonded directly or indirectly to phosphorus and such that no phosphorus atoms are bonded directly or indirectly to the same carbon atom. The basic structures of the inorganic polymer forms are shown in FIGS. 7 and 8.

When coupling is through carbon, the organophosphoric acid compound is an organo phosphonic acid and the product a phosphonate. When coupling is through oxygen-carbon, the organophosphorus acid compound is an organo-phosphoric monoester acid and the product a phosphate.

The general reaction for phosphonic acids alone is shown in equation (1) below and for monoesters of phosphoric acid alone by equation (2).

$$M^{+4}+2(HO)_2OPR \rightarrow M(O_3P-R)_2+4H^+ \tag{1}$$

$$M^{+4}+2(HO)_2OP-OR' \rightarrow M(O_3P-OR')_2+4H^+ \tag{2}$$

wherein R' is the remainder of the organo group.

The product contains phosphorus to metal in a molar ratio of about 2 to 1, and the empirical formula for the product would show all organo groups bound to phosphorus.

While nowise limiting, the R groups attachable to phosphorus may be saturated and unsaturated, substituted and unsubstituted and include, among others, alkylene, alkyloxy, alkyne, aryl, haloalykl, alkylaryl, aryloxy, mercaptoalkyl, aminoalkyl, carboxyalkyl, morpholinoalkyl, sulfoalkyl, phenoxyalkyl, beta-diketo alkyl, cyanoalkyl, cyanoalkoxy, heterocyclics and the like.

In general, the organo group should occupy no more than about 25 Å² for proper spacing. This limitation is imposed by the basic crystal structure of zirconium phosphate. Referring to FIG. 4, a spacing of 5.3 Å is shown between zirconium atoms in the zirconium plane of a crystal a total area of about 24 Å² is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 Å², adjacent groups may be somewhat larger than 24 Å² and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE 1

| Moiety | Minimum Area (Å²) |
| --- | --- |
| Alkyl chain | 15 |
| Phenyl | 18 |
| Carboxyl | 15 |
| Sulfonate | 24 |
| Nitrile | 9 |
| Morpholinomethyl | 21 |
| Trimethylamino | 25 |
| Isopropyl | 22.5 |
| t-butyl | 25 |
| Chloromethyl | 14 |
| Bromoethyl | 17 |
| Diphenylphosphine | 50 (approx.) |
| Mercaptoethyl | 13.5 |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the organophosphorus acid compounds are water soluble, an organic solvent such as ethanol may be employed, where water interferes with the reaction. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the organophosphorus acid compound may serve as a solvent. Typically, the liquid medium is the liquid medium in which the organophosphorus acid is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reaction and provide an inorganic polymer diluted in respect to the organo group in proportion to the amount of phosphorous or phosphoric acid employed.

Reaction is virtually instantaneous at all temperatures leading to precipitation of layered crystalline, semi-crystalline or amorphous inorganic polymer solid.

The amorphous phase appears as a gel similar to silica gel. The gel can be crystallized by extended reflux in the reaction medium, usually from about 5 to about 15 hours. The semi-crystalline product is characterized by a rather broad X-ray powder diffraction pattern.

The presence of sequestering agents for the metal ion slows down the reaction and also leads to more highly crystalline products. For instance, a semi-crystalline solid has been prepared by the aqueous phase reaction of zirconium oxychloride and excess 2-carboxyethyl phosphonic acid, followed by 15 hours of reflux. A highly crystalline modification was prepared under identical conditions except that hydrogen fluoride was added to the reaction mixture. A slow purge of $N_2$ over the surface of the reaction solution slowly removed the fluoride from the system. Fluoride is a very strong complexing agent for zirconium ions. The slow removal of fluoride results in slow release of the metal ion for reaction with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium and the rate of formation of this product is slow and the product polymer quite crystalline.

As compared to zirconium phosphate forming crystals of 1-5 microns, crystals of 100 to greater than 1000 micron in size have been prepared in accordance with the invention.

A property critical for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525° C., indicating remarkable stability. Decomposition of zirconium 2-carboxyethylphosphonate begins between 300° and 400° C. The decomposition process inflection point, approximate mid-point, falls at about 400° C.

While not bound by theory, phosphates probably decompose like carboxylic esters to yield acids and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis confirmed covalent bonding to phosphorus. This is because normal intercalative interactions are reversed within 10° to 100° C. above the boiling point of the guest.

The process disclosed herein permits a wide variety of inorganic polymers to be formed having the characteristic of the organo group protected by the inorganic polymer structure and, with subsequent exchange or substitution reactions, the formation of other inorganic polymers. Polymers formed may be block, random and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphite phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, this band was shifted to 2440 cm$^{-1}$ and broadened.

Another route is to exchange one pendant group for another. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction such as

where as in FIG. 6, ⊔⊔⊔⊔⊔⊔ represents the interlamellar layer to which the alkyl group is anchored. As with all organo groups, for the bis configuration at least two carbon atoms are present, preferably from two to twenty atoms, and the phosphorus atoms are linked directly or indirectly to different carbon atoms. Since size of the linking group will control and fix interlamellar spacing, there is provided effective laminar sieves of fixed spacing for application analogous to that of molecular sieves.

Ion exchange activity has been established with pendant carboxylic acid groups. Prepared zirconium 2-carboxyethyl phosphonate was established to have an interlayer distance of 12.8 Å. When intercalated to form its n-hexylammonium salt interlayer distance increased to 27.2 Å. When sodium was taken up, layer spacing increased to 14.2 Å. X-ray and infrared data indicated the highly crystalline inorganic polymer to behave as expected for carboxylic acid with behavior analogous to ion exchange resins except that both external and internal surfaces were functional, establishing them as super surface ion exchange resins. Moreover, since the inorganic polymers can be prepared as microcrystalline powders, diffusion distances are short.

As summarized in Table 1, nitrile and mercapto anchored groups show the ability to take up silver and copper ions at room temperature for catalytic activity.

TABLE II

| Anchored Group | Metal Ion | Loading | mMole Metal mMole Zr |
|---|---|---|---|
| —O ~ CN | 0.1 M Ag$^+$ | | 0.20 |
| ~ SH | 0.1 M Ag$^+$ | | 1.00 |
| —O ~ CN | 0.1 M Cu$^{++}$ | | 0.10 |
| —O ~ CN | 0.1 M Cu$^{++}$ | 0.5 M HOAc 0.5 M NaOAc | 0.10 |

~ = groups formed of carbon and hydrogen.
OAc = acetate radical.

The alternate to catalytic utility is to attach the metals to the organophosphorus acid prior to reaction with the soluble tetravalent metal compound.

The high surface area of the crystalline products also make them utile for sorption of impurities from aqueous and non-aqueous media.

Another utility is as an additive to the polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and to elevate heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals, substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from suppliers. The products formed are insoluble in normal solvents and do not sublime. However, the combined weight of yield data, spectroscopy, elemental analyses and powder diffraction results confirm the compositions reported with good reliability.

EXAMPLE I

Preparation of: Zr(O$_3$PCH$_2$Cl)$_2$

Into a reaction flask was introduced a solution of 5.500 g of ZrOCl$_2$.8H$_2$O dissolved in 80 ml of water. To this solution was added, with stirring, a mixture of 46 ml of an aqueous solution that was 85 percent by weight H$_2$PO$_3$CH$_2$Cl and 4 ml of a 40 percent by weight aqueous solution of hydrofluoric acid. A precipitate formed upon mixing the solutions. The reaction mixture was refluxed at about 100° C. over a weekend to enhance crystal growth and layering within the crystal structure.

Following refluxing, the reaction mixture was filtered to separate the solid precipitate from the liquid. The solid separated was washed with successive washes of water, acetone and ether. The washed solid was then dried in an oven at 50° C. for about one hour. The weight of solid recovered was 5.898 g, which was about a 99.1 percent yield as the theoretical yield for the product $Zr(O_3PCH_2Cl)_2$ was 5.947 g.

Upon infrared analysis and X-ray diffraction analysis the precipitate recovered was shown to be layered $Zr(O_3PCH_2Cl)_2$.

Elemental analysis of the recovered product provided the following results: 6.53% C; 1.26 H; and 17.38% Cl. An X-ray powder diffraction pattern showed the compound to be crystalline having an interlayer spacing of 10.0 Å.

EXAMPLE II

Preparation of: $Th(O_3PCH_2Cl)_2$

The technique of Example I was repeated in every essential detail with the exception that to the reaction flask was added 10.22 g of an aqueous solution of about 85 percent $H_2PO_3CH_2Cl$ and a solution of 6.619 g of $Th(NO_3)_4.4H_2O$.

Upon mixing the solutions, a white precipitate formed almost immediately. The reaction mixture was then refluxed for about a day to enhance the layered structure of the crystals formed.

Following refluxing, the solid precipitate was separated from the liquid by filtration. The recovered solid was washed with successive washes of water, acetone and ether. The resulting solid was allowed to dry in an oven at about 55° C.

Upon infrared analysis, the solid was shown to be $Th(O_3PCH_2Cl)_2$.

Elemental analysis of the recovered product provided the following results: 4.62% C; 1.46 H; and 12.65% Cl. An X-ray powder diffraction pattern showed the compound to be crystalline having an interlayer spacing of 10.5 Å.

EXAMPLE III

Preparation of: $Pb(O_3PCH_2Cl)_2$

The technique of Example I was repeated in every essential detail with the exception that an aqueous solution containing 3.892 g of $Pb^{IV}O_2$ was introduced into the reaction flask. Also added to the reaction flask was 12.264 g of an aqueous 85 percent by weight solution of $H_2PO_3CH_2Cl$ which was about a 2.5 fold excess over the lead oxide.

The reaction mixture was heated for a few days. During this time a precipitate formed. The precipitate was separated from the liquid by filtering. The solid precipitate recovered was washed with successive washes of water, acetone and ether. The precipitate was then dried in an oven at about 55° C. for a few hours. The solid recovered was a fine light brown powder and had a weight of 5.092 g. The theoretical yield of $Pb(O_3PCH_2Cl)_2$ was 7.55 g.

Elemental analysis of the recovered product provided the following results: 3.65% C and 7.2% H. An X-ray powder diffraction pattern showed the compound to be crystalline having an interlayer spacing of 9.83 Å.

EXAMPLE IV

Preparation of: $Ti(O_3PCH_2Cl)_2$

To a reaction flask was added 4.735 g of an aqueous solution containing 85 percent by weight $H_2PO_3CH_2Cl$ which provided 4.025 g of $H_2PO_3CH_2Cl$. Also introduced into the reaction flask was 14.790 g of an aqueous solution that was 30 percent by weight $TiCl_4$. The titanium chloride was utilized in about a one and one-half fold excess over the $H_2PO_3CH_2Cl$. Also added to the reaction flask was 10 ml of water.

Upon mixing the solutions, a gel-like precipitate formed. The reaction mixture was refluxed overnight to enhance layering of the $Ti(O_3PCH_2Cl)_2$. Following refluxing, the reaction mixture was filtered to recover the precipitate formed. The recovered precipitate was washed with successive washes of water, acetone and ether. The washed precipitate was then oven dried at about 55° C. for about four hours. The weight of the dried solid was 5.891 g.

Elemental analysis of the recovered product provided the following results: 6.37% C; 2.79% H; 16.36% Cl. An X-ray powder diffraction pattern showed the compound to be semicrystalline to amorphous having an interlayer spacing of 11.8 Å.

EXAMPLE V

Preparation of: $Zr(O_3PCH_2CH_2N^+H_3{}^-Cl)_2$

In a reaction flask containing about 50 ml of water was added 0.504 g of $H_2O_3PCH_2CH_2N^+H_3{}^-Cl$, and 0.638 g of $ZrOCl_2.8H_2O$. Also added to the reaction flask was 1 ml of a 38 percent hydrochloric solution.

A precipitate appeared slowly after about one-half hour following the mixing of the reactants. The reaction mixture was refluxed for about one day to enhance layering of the crystal structure in the precipitate. Following refluxing the precipitate formed was recovered by filtering. The recovered solid was washed with successive washes of water and acetone. The solid was then allowed to dry at about 45° C. in an oven. The amount of solid recovered was 0.824 g which was determined to be $Zr(O_3PCH_2CH_2N^+H_3{}^-Cl)_2.\tfrac{1}{4}H_2O$.

Elemental analysis of the recovered product provided the following results: 11.98% C; 4.67 H; 6.45% O. An X-ray powder diffraction pattern showed the compound to be semicrystalline having an interlayer space of 14.3 Å.

The product as produced has utility as an anion exchanger and when the product is converted to its free base form it has utility as a metal ion complexer.

EXAMPLE VI

Preparation of: $Zr(O_3PCH_2CH_2CH_2PO_3)$

In a reaction vessel was dissolved 0.787 g of propylene diphosphonic acid

in about 20 ml of water. This amount of propylene diphosphonic acid was an amount in a slight stoichiometric excess over the $ZrOCl_2$.

A solution was also prepared in 0.681 g of $ZrOCl_2$ dissolved in about 10 ml of water. This solution was added, with stirring, to the propylene diphosphonic acid solution. A white precipitate appeared almost immediately upon mixing the two solutions.

To the reaction mixture was added 3 ml of 38 percent hydrochloric acid and water to adjust the total volume of the reaction mixture to about 50 ml. The reaction mixture was then refluxed for about eight hours in a flask equipped with a reflux condenser. The condenser was provided with a trap for the vapors lost through the condenser to prevent acid vapors from escaping. The vapors emitted from the condenser were directed to a trap-containing dilute sodium hydroxide.

Following refluxing the reaction mixture, the mixture was filtered to recover the solid precipitate that formed during refluxing. The solid precipitate recovered was washed successively with water and acetone and allowed to air dry. Following air drying, the precipitate weighed 1.113 g. The precipitate was then dried in an oven at about 80° C. for about three hours. The resultant precipitate then had a weight of 1.050 g.

Elemental analysis of the recovered product provided the following results: 12.70% C; 3.58% H; ; 20.7% P. An X-ray powder diffraction pattern showed the compound to be amorphous.

EXAMPLE VII

Preparation of: $Ti(O_3PCH_3)_2$

In a 100 ml round-bottom flask containing 40 ml of water was added 0.913 g of $H_2O_3PCH_3$. To the resultant solution was added 2.133 g of an aqueous solution that was 30 percent by weight $TiOCl_2$ which was slightly less than a stoichiometric amount of the phosphonic acid. Also added to the flask was 2 ml of 38 percent hydrochloric acid. The total volume of the solution was about 60 ml.

Upon the addition of the $TiOCl_2$ solution, no apparent reaction occurred. After about five minutes had elapsed, a haze appeared and developed into a white gel-like precipitate. The reaction mixture was then refluxed overnight (about 20 hours). During refluxing the flask was fitted with a reflux condenser and the vapors emitted from the condenser were directed to a sodium hydroxide scrubber.

After refluxing, the precipitate formed was separated from the liquid by filtering. The recovered precipitate was washed with successive washes of water, acetone and ether. The amount of solid recovered was 19.5 g. The solid was dried in an oven at a temperature of about 85° C. for about one hour, which resulted in a weight of 0.919 g.

Elemental analysis of the recovered product provided the following results: 6.54% C; 4.54% H; 17.5% P. An X-ray powder diffraction pattern showed the compound to be amorphous.

EXAMPLE VIII

Preparation of: $Th(O_3PCH_3)_2$

Into a reaction flask was placed about 15 ml of water and 0.845 g of $H_2O_3PCH_3$, which was dissolved in the water. To the reaction flask was added an aqueous solution containing 2.252 g of $Th(NO_3)_4 \cdot 4H_2O$. This solutiom was added to the phosphonic acid solution.

No precipitate appeared upon the mixing of the two solutions. After about one hour had elapsed from the initial mixing, a haze appeared which developed within about 15 minutes into a precipitate.

The reaction mixture was then reluxed for about four hours. Following refluxing, the reaction mixture was allowed to cool to room temperature and the solid precipitate was recovered by filtering. The recovered solid was washed with successive washes of water and acetone and allowed to air dry. The solid, after air drying, weighed 1.766 g. The precipitate was then dried in an oven for about one hour at 100° C. After drying, the precipitate weighed 1.704 g providing a yield of $Th(O_3PCH_3)_2$ of about 99.5 percent.

Elemental analysis of the recovered product provided the following results: 4.78% C; 2.21% H; 51.4% Th. An X-ray powder diffraction pattern showed the compound to be crystalline, having an interlayer spacing of 8.92 Å.

EXAMPLE IX

Preparation of: $Zr(O_3PCH_3)_2$

Into a reaction vessel was placed 20 ml of water and 0.814 g of

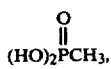

$(HO)_2PCH_3$, which was dissolved in the water. An aqueous solution containing 0.751 g of $ZrOCl_2$ was added to the phosphonic solution.

Upon mixing the solutions, a gel-like precipitate appeared. One milliliter of 38 percent hydrochloric acid was added and the volume of the reaction mixture was increased to about 50 ml by the addition of water. The reaction mixture was then refluxed to enhance layering of the crystal structure of the precipitate.

After refluxing the reaction mixture for about four hours, the reaction mixture was allowed to cool. The mixture was filtered to recover the precipitate which had formed during refluxing. The recovered solid was washed with successive washes of water and acetone. The solid was then dried for about one hour at 100° C. The solid weighed 0.867 g.

Elemental analysis of the recovered product provided the following results: 8.84% C and 2.95% H. An X-ray powder diffraction pattern showed the compound to be amorphous.

EXAMPLE X

Preparation of: $Th(O_3PC_{18}H_{37})_2$

Dimethyl octadecyl phosphonate was hydrolyzed to provide octadecyl phosphonic acid. The octadecyl phosphonic acid was formed by reacting 0.952 g of dimethyl octadecyl phosphonate

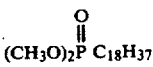

$(CH_3O)_2P\ C_{18}H_{37}$ with 13 ml of a 48 percent hydrobromic acid solution and heating the mixture to produce methyl bromide, $CH_3Br$, as a gas and octadecyl phosphonic acid

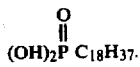

$(OH)_2P\ C_{18}H_{37}.$

The reaction mixture was refluxed for about three-fourths of an hour to evolve the methyl bromide. The reaction was complete when the evolution of methyl bromide ceased. About 15 ml of toluene was added to dissolve the octadecyl phosphonic acid and any remaining diester. The reaction mixture was again refluxed an additional three-fourths of an hour to ensure the completion of the hydrolysis reaction.

After hydrolysis, 0.726 g of Th(NO₃)₄.4H₂O (about a stoichiometric amount), was dissolved in methanol and water and added to the reaction flask containing the octadecyl phosphonic acid. Upon mixing no precipitate appeared. An additional volume of toluene was added to the reaction mixture and the reaction mixture was refluxed overnight.

Following refluxing, the reaction mixture was cooled to room temperature. A haze, which had developed in the toluene layer during refluxing, was recovered by filtering. The haze was recovered upon filtering as a waxy solid which exhibited a waxy character different from the initial reactants. The solid was washed with methanol and air dried over the weekend. The solid recovered weighed 1.100 g, which was about a 93.4 percent yield of Th(O₃PC₁₈H₃₇)₂.

Elemental analysis of the recovered product provided the following results: 46.57% C; 8.43% H; 20.9% Th. An X-ray powder diffraction pattern showed the compound to be crystalline, having an interlayer spacing of 42 Å.

EXAMPLE XI

Preparation of:

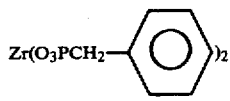

In a reaction flask was placed 1.035 g of ZrOCl₂ dissolved in a solution of about 90 percent THF and 10 percent water. Introduced into the reaction flask was a solution containing 2.002 g of

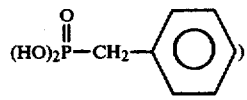

dissolved in a solvent that was about 90 percent THF and 10 percent water.

A white precipitate formed quickly upon mixing the solutions. The reaction mixture was refluxed, with stirring, for about eight hours. After refluxing, the reaction mixture was cooled and filtered to recover the precipitate which had formed. The solid recovered was washed with acetone and air dried. The resultant solid weighed 2.280 g and was white in color and chalky in appearance. The percentage yield of

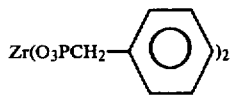

was 92 percent.

Elemental analysis of the recovered product provided the following results: 30.01% C and 3.96% H. An X-ray powder diffraction pattern showed the compound to be semicrystalline, having an interlayer spacing of 14.7 Å.

EXAMPLE XII

Preparation of: Zr(O₃PCH₂CH=CH₂)₂

Into a 125 ml Erlenmeyer flask was placed 9.900 g of

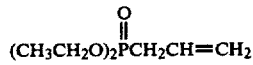

which was reacted with 36 g (about a two-fold excess) of 48 percent hydrobromic acid to hydrolyze the ester. The reaction mixture was refluxed for about 45 minutes and ethyl bromide was evolved and collected. After the hydrolysis reaction had been completed as evidenced by the collection of ethyl bromide, the refluxing was discontinued.

About 75 percent of the hydrolyzed solution containing the phosphonic acid

(0.0417 moles) was diluted with about 50 ml THF and a small amount of water. To the solution was added, with stirring, 3.690 g ZrOCl₂ (0.0209 moles) dissolved in about 10 ml of water.

A precipitate appeared very quickly upon mixing. The solution was then refluxed for about one hour and heated to a temperature below reflux for overnight. The reaction mixture was allowed to cool and was filtered to separate the precipitate which had formed during reflux and heating. The precipitate recovered was a white solid and was washed with successive washes of water, acetone and ether. When the ether was added to the solid on the filter, the packed solid dispersed quickly giving a separation into two layers. The bottom layer was clear and contained mostly water and acetone. The upper layer (the ether layer) contained the solid precipitate. The solid was then dried at about 100° C. for about one hour. The resultant solid weighed 5.703 g, which provided about an 83 percent yield of Zr(O₃PCH₂CH=CH₂)₂.

The infrared analysis of the precipitate showed a strong C=C stretch characteristic peak at 1650 cm⁻¹, a C—H vinyl stretch and C—H alkyl stretch at 3000 cm⁻¹, and characteristic peaks for P—O and P=O at 900 to 1200 cm⁻¹.

Elemental analysis of the recovered product provided the following results: 20.5% C and 3.56% H. An X-ray powder diffraction pattern showed the compound to be amorphous.

EXAMPLE XIII

Preparation of:

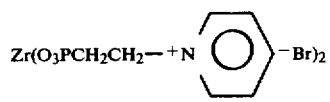

Into a reaction flask was placed 5.000 g of

which was mixed, with stirring, with 5 ml of pyridine and 10 ml of benzene. The pyridine was present in about a three-fold excess over the ester. The reaction mixture was heated mildly with a heating mantle (variac setting 20) for about eight hours, with stirring, to produce

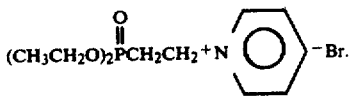

The reaction mixture was stripped of benzene and most of the unreacted pyridine on a rotary evaporator at a temperature of about 100° C. A heavy oil residue was left after stripping which, upon NMR analysis, showed the oil to be about 20 percent pyridine and about 80 percent

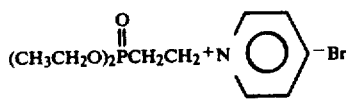

and containing trace amounts of other impurities. The weight of the oil was 7.9 g which, at 80 percent purity, correlated to 6.32 g of the pyridine salt

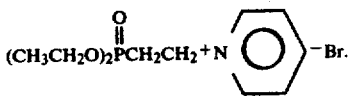

The pyridine salt was hydrolyzed with 15 g of concentrated 48 percent hydrobromic acid. The reaction mixture was refluxed for about 2.5 hours to produce the pyridine salt-phosphonic acid

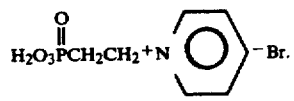

The reaction mixture was allowed to cool and following cooling there was added about 15 g of a 48 percent hydrobromic acid solution and 1.736 g of ZrOCl₂ dissolved in water. A sufficient amount of ZrOCl₂ was added to complex all of the pyridine salt-phosphonic acid to

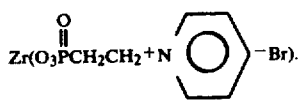

Upon addition no precipitate appeared. To the reaction mixture was added THF which, upon addition initiated precipitation of a solid.

The reaction mixture was cooled in an ice water bath to obtain additional precipitate. The reaction mixture was then filtered and the recovered solid washed with ether. The solid recovered was dried at about 90° C. for about one hour and, upon drying, changed from a white to orange color. The amount of solid recovered was 4.61 g. The theoretical yield was 6.08 g.

A portion of the precipitate was dissolved in D₂O and an NMR analysis taken. The NMR spectrum matched that for

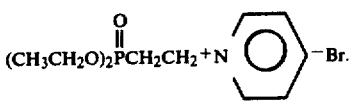

However, the lines on the NMR spectrum for the precipitate were quite broad and fine splitting was observed in the spectrum of the ester. The broad lines indicated the possibility of a fine dispersion such as occurs by the spreading of molecular platelets in a layered compound.

An X-ray powder diffraction pattern showed the compound to be amorphous. The product can be used as an anion exchanger.

EXAMPLE XIV

Preparation of: Zr(O₃P(CH₂)₁₀PO₃)

In a reaction flask was placed 15.05 g of

which was reacted with 32 ml of a 48 percent hydrobromic acid having a density of 1.483 g/ml. The hydrobromic acid was present in about a 100 percent excess over the biester. The two solutions were mixed and heated to reflux the solution. The reaction flask was a round bottom flask fitted with a Dean-Stark trap for collecting ethyl bromide and a condenser. After 1.5 hours of vigorous refluxing, about 9.80 ml of ethyl bromide had been collected, which corresponded to about 90 percent completion of the hydrolysis reaction. The liquid product remaining in the flask was the bisphosphonic acid,

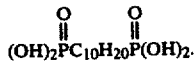

The bisphosphonic acid was dissolved in methanol to make a solution having a total volume of about 250 ml. This solution had a concentration that was about 0.145 moles per liter of the bisphosphonic acid. Twenty-five milliliters of the bisphosphonic acid solution (3.6 mM) was reacted with a solution of 0.64 g ZrOCl₂(3.6 mM) in 10 ml of water and 40 ml of methanol. A thick white precipitate formed upon mixing the solutions. The reaction mixture was refluxed for three hours to enhance layering of the crystal structure of the precipitate. After refluxing, the reaction mixture was filtered to recover the precipitate. The precipitate was air dried to a constant weight of 1.27 g. The theoretical yield was 1.4 g which provided a percentage yield of 91 percent. A microscopic inspection of the initial precipitate formed upon adding the bisphosphonic acid in methanol to the ZrOCl₂ in methanol/water showed sheet-like delicate fragments.

Elemental analysis of the recovered product provided the following results: 31.22% C and 6.11% H. An X-ray powder diffraction pattern showed the compound to be semicrystalline to amorphous, having an interlayer spacing of 17.3 Å.

EXAMPLE XV

Preparation of: $Zr(O_3PCH_2CH_2PO_3)$

Into a 250 ml three-necked flask was introduced 22 g of the bisester of

$(CH_3CH_2O)_2\overset{O}{\overset{\|}{P}}CH_2CH_2\overset{O}{\overset{\|}{P}}(OCH_2CH_3)_2$ (70.1 mM) and 94.6 g of 48 percent aqueous hydrobromic acid. The reaction flask was fitted with a magnetic stirrer, reflux condenser, Dean-Stark trap and thermometer. The temperature of the solution was raised to about 105° C. Smooth evolution of ethyl bromide was observed commencing at about a temperature of 85° C. At a temperature of about 85° C. there was less than 0.5 ml of ethyl bromide collected. At a temperature of about 95° C. there was about 10 ml ethyl bromide collected, at about 103° C. there was about 16 ml collected and at a temperature of about 110° C. there was about 20 ml of ethyl bromide collected. Following the hydrolysis reaction, the reaction mixture was cooled to room temperature. There was then added 5.6 g of $ZrOCl_2.8H_2O$ (17.3 mM) dissolved in about 5 ml of water. Upon mixing the solutions a precipitate appeared almost immediately. The mixture was then brought to a gentle reflux and allowed to reflux overnight.

Following refluxing, the mixture was cooled to room temperature and filtered on a fine fritted funnel to collect the precipitate which had formed during refluxing. The filtrate (82.6 g) containing unreacted bisphosphonic acid was collected. The white solid precipitate product recovered was washed with about 50 ml of deionized water. The wet, pasty cake from the water wash was slurried in acetone and filtered. The solid was then suction filtered and air dried and oven dried for about 15 hours at 100° C. The dried solid weighed 5.16 g.

EXAMPLE XVI

Preparation of: $Zr(O_3PCH_2CH_2CL)_2$

To a resin kettle fitted with a heating mantle was added 78.248 g of

$(HO)_2\overset{O}{\overset{\|}{P}}CH_2CH_2Cl$ as a 21.6 percent aqueous solution. 22.18 g of a 48 percent aqueous solution of hydrochloric acid was also added to the resin kettle. To the resin kettle was then added 94.64 g of $ZrOCl_2$ dissolved in about 200 ml of deionized water. The heating mantle was turned on at a variac setting of 70 V. A precipitate formed almost immediately upon addition of the $ZrOCl_2$ solution. A Dean-Stark trap was added and the reaction mixture was then refluxed overnight (about 22 hours) to provide layering of the crystal structure formed in the precipitate.

Following refluxing, the reaction mixture was filtered through a fine frit funnel. The precipitate recovered was washed with successive washes of deionized water, acetone and ether. Following the ether wash, the precipitate was allowed to air dry and then was oven dried at a temperature of about 105° C. for about two hours. The weight of the $Zr(O_3PCH_2CH_2Cl)_2$ recovered was 134.96 g which provided about a 67.48 percent yield of the product.

EXAMPLE XVII

Preparation of: $Zr(O_3PCH_2CH_2Br)_2$

To a 250 ml three necked round bottom flask was added 24.5 g (19.2 ml) of

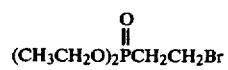
$(CH_3CH_2O)_2\overset{O}{\overset{\|}{P}}CH_2CH_2Br$ (0.10 mole) and 67 g of an aqueous 48 percent hydrobromic acid (0.40 moles). The flask was then fitted with a mechanical stirrer, Dean-Stark trap, reflux condenser and thermometer. The mixture was heated to about 90° C. to hydrolyze the ester. At about 90° C. ethyl bromide was evolved. After about four hours about 15 ml of ethyl bromide had been collected in the trap. The remaining aqueous solution in the round bottom flask weighed about 68 g. Thirty-two grams of water was added to the solution in the flask to provide 0.1 moles of the phosphonic acid

$(HO)_2\overset{O}{\overset{\|}{P}}CH_2CH_2Br.$

Fifty grams of the solution of the phosphonic acid

$(HO)_2\overset{O}{\overset{\|}{P}}CH_2CH_2Br$ (0.05 moles) was charged to a 250 ml three necked round bottom flask fitted with a magnetic stirrer and slow nitrogen purge. To the flask was added a solution of 6.2 g of $ZrOCl_2.8H_2O$ in 20 ml of water. A precipitate appeared almost immediately upon mixing the two solutions. The reaction mixture was heated to a gentle reflux under a slow nitrogen purge for about four hours. Following refluxing the reaction mixture was cooled to room temperature and the white solid precipitate that had formed during refluxing was filtered on a fine filter and washed once with water, twice with acetone and twice with ether. The precipitate was then oven dried. After oven drying the recovered precipitate weighed 8.6 g.

EXAMPLE XVIII

Preparation of: $Zr(O_3PCH_2CH_2CN)_2$

To a reaction vessel was added 6.365 g (0.0400 moles) of

$(CH_3CH_2O)_2\overset{O}{\overset{\|}{P}}CH_2CH_2CN.$

Also to the reaction flask was added 12 ml of $(CH_3)_3SiI$. The reactants were allowed to react for about two hours. After about two hours 10 ml of water was added to the flask followed by an additional 20 ml of water. As the water was added, a frothing appeared in the flask. After the frothing subsided, an organic layer appeared below the aqueous layer. The layers were separated and the lower organic layer collected and saved.

The solution of 6.035 g $ZrOCl_2.8H_2O$ was dissolved in 25 ml of water and added dropwise to the collected organic layer, the cyanophosphonic acid solution. The cyanophosphonic acid solution was chilled to about 9° C. during the addition of the $ZrOCl_2$. As the two solutions were mixed, a precipitate occurred almost immediately. The reaction mixture was allowed to react at room temperature for about 48 hours.

The reaction mixture was filtered to collect the precipitate which had formed. The solid precipitate recovered by filtering was washed with three successive washes of water (100 ml, 75 ml and 150 ml). The precipitate was then washed with two separate 100 ml washes of acetone and then was washed with two successive washes of ether. The precipitate was then air dried. The recovered precipitate weighed 6.450 g which was a yield of product of about 90.26 percent.

Elemental analysis of the recovered precipitate provided the following results: 18.72% C; 2.28% H; and 7.30% N. An X-ray powder diffraction pattern showed the compound to be crystalline having an interlayer spacing of 11.79 Å.

EXAMPLE XIX

Preparation of:

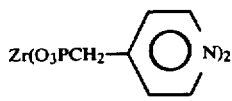

To a reaction flask is introduced 75 ml of an aqueous solution containing

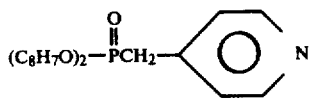

(0.00397 moles). The flask was provided with a stirrer and was placed in an ice bath. The reaction flask was purged with nitrogen. To the flask was added 4.75 ml of $(CH_3)_3SiI$. The trimethyl silyl iodide was added from a graduated funnel over a period of about 15 minutes. During the addition the solution changed from pale to a strong yellow color. After the 15 minute addition time, holding the solution at 0° C., the solution became cloudy indicating that silation had occurred at the nitrogen. An additional 2.5 ml of trimethyl silyl iodide was added dropwise over a 15 minute period to react with the ethyl groups. The reaction temperature was maintained from about 0° to 15° C. The solution then contained

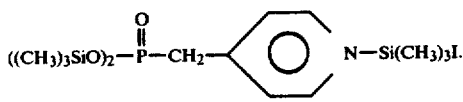

The solution contained a precipitate and it was, therefore, difficult to determine whether a solid had formed. The solution was then divided into two separate flasks containing equal volumes of the reaction mixture.

To the first portion of the reaction mixture was added 2.300 g of $Zr(OC_3H_7)_4$. A solid phase was produced. The solid was separated by filtering through a fritted disc. The amount of solid product collected was 0.166 g. This amount of product recovered was a yield of about 19.2 percent.

A sample of the product was analyzed by infrared analysis. The analysis indicated that there were some P—O—C and C≡N present in the product.

The product can be used as a metal ion complexer. When the product is converted to its quaternized form it can be used as an anion exchanger.

EXAMPLE XX

Preparation of: $Zr(O_3PCH_2CH_2CO_2H)_2$

To a 500 ml round-bottom flask fitted with a Claisen head, reflux condenser, thermometer and magnetic stirrer, was added 68 g (48 ml, 0.376 moles) of $BrCH_2CH_2CO_2CH_2CH_3$ and 130 g (162 ml, 0.78 moles) of triethylphosphite. The temperature of the reaction mixture was raised to 140° C., at which time evolution of ethyl bromide began. The ethyl bromide was collected in a trap at 0° C. The temperature of the reaction mixture was raised slowly to about 170° C. over two hours. Evolution of ethyl bromide continued. A slow nitrogen purge was maintained on the system to displace the ethyl bromide to the trap.

A gas chromatographic sample taken after two hours indicated that most of the bromine ester had reacted. The reaction mixture was distilled under a vacuum. A first fraction was collected having a boiling point of about 35° C. at 2 mm Hg. This fraction was mostly dry ethylphosphate. A second fraction was collected having a boiling point within the range of 35° C. to about 70° C., at a pressure of 0.05 mm Hg. This fraction was considered to be a mixture of dry ethylphosphite and $Br(CH_2CO_2CH_2CH_3)$. A third fraction was collected having a boiling point of about 78° to 85° C., at a pressure of 0.05 mm Hg. A fourth fraction was collected having a boiling point of 85° to 90° C., at a pressure of 0.05 mm Hg. The last two fractions were combined since neither contained significant triethylphosphite. The combined fractions were the ester

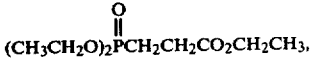

which product weighed 87 g.

The ester was hydrolyzed by placing 80 g in a 500 ml three-necked flask. To the flask was added 100 ml of a 47 percent by weight hydrobromic acid solution. The solution was stirred and the flask was fitted with a Dean-Stark trap. As the temperature was raised with a heating mantle, ethyl bromide evolution began. The temperature was raised slowly to about 110° C. The distillate was collected and was shown to be both ethanol and ethyl bromide. After about 90 ml of the distillate had collected, having a boiling point of less than 100° C., a pale yellow solution remained in the flask. The solution weighed about 134 g and had a volume of about 100 ml. The product in the solution was the phosphonic acid,

The phosphonic acid solution (21.8 ml), which was about 11.1 g (72 mM), was charged to a 250 ml round-bottom flask. To the flask was added 25 ml of water. To this clear solution was added 9.20 g of ZrOCl$_2$.8H$_2$O (28.5 mM) dissolved in 10 ml of water. Upon mixing, a white precipitate appeared almost immediately. An additional 17 ml of water was added to fluidize the system. The temperature was then raised to gently reflux the reaction mixture. Following refluxing, the heat was removed and the reaction mixture was allowed to cool.

The white solid which had precipitated during the refluxing was separated from the slurry by filtering. The recovered solid was washed with acetone and ether and air dried to a constant weight. The weight of the dry white powder was 12.1 g. The weight of the sample approximated that of the 1.5 hydrate of Zr(O$_3$PCH$_2$CH$_2$CO$_2$H)$_2$.

Elemental analysis conducted on the precipitate had the following results: 10.63% C; 3.45% H; and 13.1% P. An X-ray powder diffraction pattern showed the compound to be crystalline.

EXAMPLE XXI

The usefulness of the zirconium 2-carboxy ethyl phosphonate formed in Example XX was shown in an experiment which tested the ability of the compound to extract copper ions from aqueous solutions.

In the experiment, 1.00 g of the zirconium 2-carboxy ethyl phosphonate was mixed with 40 ml of 0.103 M copper solution having a pH of 4.01 and, after about 30 minutes, a 10 ml aliquot of the solution phase was removed and labeled as 1201-29-1, its pH being 2.19. The remaining slurry was treated with 4 ml of 2.5 percent of sodium hydroxide solution and, after about 10 minutes, the liquid, with a pH of 3.93, was removed and labeled 1201-30-1. A second 1.11 g portion of the zirconium 2-carboxy ethyl phosphonate was mixed with 40 ml of the 0.103 M copper solution, and 2.0 ml of 2.5 percent sodium hydroxide solution was added. After about 15 minutes, a 10 ml aliquot of the supernatant liquid, which had a pH of 3.39, was removed and labeled 1201-31-1. The remaining slurry was treated with 5.0 ml of 2.5 percent sodium hydroxide solution and after about 30 minutes, the supernatant liquid having a pH of 4.85 was removed and labeled 1201-32-1.

A loading curve was obtained for the solution of zirconium 2-carboxy ethyl phosphonate. The loading curve was prepared by plotting the pH of the solution versus the milli equivalents of copper extracted per gram of zirconium 2-carboxy ethyl phosphonate.

EXAMPLE XXII

To a one liter, three-necked flask fitted with a stirrer, addition funnel, reflux condenser and thermometer, was charged 225 ml of dry toluene. A 17.2 g portion of 57 percent by weight sodium hydride dispersion (in mineral oil) was added with stirring.

Diethylphosphite (56.5 g) was placed in the addition funnel and added dropwise, over about two hours, to the toluene slurry. A smooth evolution of hydrogen began immediately. The addition rate was periodically adjusted to control the foam level in the reactor. Slurry temperature was between 30°-40° C. during the addition.

After addition of all the diethylphosphite, a solution of 52 g 1,3-propane sultone in 20 ml of toluene was placed in the addition funnel, and added to the reaction mixture at a rate of about 1 ml per minute. During this addition, the temperature of the reaction mixture rose to about 60° C. The mixture was cooled to room temperature while standing overnight.

Two phases were present in the reaction mixture. The upper clear toluene phase was decanted off and the lower viscous product phase washed with two 100 ml portions of diethyl ether. The product, which had a pasty character was placed in a glass Soxhlet extraction apparatus and continuously extracted with diethyl ether for about 40 cycles over about six hours.

The product, diethyl-3-sulfopropylphosphonate, sodium salt, was dried under vacuum and weighed 73 g, a yield of 63 percent of the theoretical weight. This product is a hygroscopic solid.

A 7.7 g portion of diethyl-3-sulfopropylphosphonate, sodium salt, was placed in a 250 ml round-bottom flask fitted with a reflux condenser and a Dean-Stark trap. To this was added 30 ml of 48 percent by weight hydrobromic acid and the solution was refluxed. Ethyl bromide was removed in the trap, and the desired hydrolysis product, 3-sulfopropylphosphonic acid, remained in the aqueous solution and was transferred to a 250 ml three-necked flask fitted with an addition funnel.

A solution of 3.3 g ZrOCl$_2$.8H$_2$O in 10 ml of water was placed in the addition funnel and added dropwise to the phosphonic acid solution while the temperature was increased to boiling. A white precipitate formed very rapidly. The mixture was heated to a gentle reflux and maintained overnight.

After cooling to room temperature, the product was isolated by filtration and washed with four 25 ml portions of acetone and two 25 ml volumes of diethyl ether.

This product, zirconium 3-sulfopropylphosphonate, was highly crystalline.

EXAMPLE XXIII

The ion exchange capability of the product in Example XXII was demonstrated for both the sulfonic acid and sodium sulfonate forms of that compound.

A 0.50 g portion of the acid form was slurried with 10 ml of 0.215 N copper sulfate solution. The pH of the solution was initially 3.80 but immediately dropped to 0.92, the initially white solid became a pale blue color, and the blue solution color decreased markedly in intensity. Atomic absorption analysis of the solution after exchange indicated a copper concentration of 0.093 N, for copper loading in the solid of 2.46 meq/g, or 77 percent of the theoretical capacity.

The exchange experiment was repeated with the sodium sulfonate form of the compound. After exchange, the solution had a pH of 2.88 and a copper content of 0.135 N. Loading of the solid was calculated as 1.62 meq/g, or 51 percent of the theoretical capacity.

EXAMPLE XXIV

Preparation of: Ar(O$_3$P(CH$_2$)$_{10}$PO$_3$)$_{\frac{1}{2}}$(O$_3$POH)$_{\frac{3}{2}}$ A stock solution of bisphosphonic acid was prepared by reacting 15.05 grams of

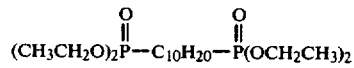

with 32 milliliters of 48 percent solution of hydrogen bromide. The hydrogen bromide was present in about 100 percent excess. The two solutions were mixed and heated to reflux in a round bottom flask fitted with a Dean-Stark trap for collecting ethyl bromide and a condenser. After about 15 hours of vigorous refluxing the reaction was about 90 percent complete as evidenced by the collected ethyl bromide. The reflux liquid provided the stock solution of bisphosphonic acid

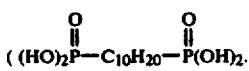

A solution was prepared by dissolving 1.92 grams of $ZrOCl_2$ (10.8 mM) in 10 ml of water and 40 ml of methanol. To this solution was added 25 ml of the stock solution of bisphosphonic acid (3.6 mM) to which had been added 1.66 grams of 85 percent phosphoric acid (14.10 mM).

The reaction mixture was then refluxed for about two and one-half hours. The mixture was then filtered to separate the formed precipitate. The precipitate was air dried to a weight of about 5.9 grams. The precipitate was then dried at about 60° C. for three hours

EXAMPLE XXV

The mixed component product of Example XXIV was shown to be very selective in its complexative absorption of amines by virtue of the ten carbon cross-links from one layer to the next. This behavior is a form of "molecular sieving."

In four separate experiments the behavior of two —OH containing zirconium phosphate layered solids toward two different amines was investigated. The two amines were a bulky trioctylamine and a small ethylamine. As the table below indicates, the noncross-linked zirconium phosphate picked up both amines from a methanolic solution. However, the product of Example XXIV picked up only the small amine, due to the constricting effect of the bridging ten carbon group.

TABLE
ABSORPTION OF AMINES

| Solid | Amine | Molar Ratio of Amine/—OH Group in Product |
|---|---|---|
| $Zr(O_3P—OH)_2$ | $C_2H_5NH_2$ | 0.86 |
| $Zr(O_3P—OH)_2$ | $(C_8H_{17})_3N$ | 0.24 |
| $Zr(O_3P(CH_2)_{10}PO_3)_{\frac{1}{2}}(O_3POH)_1$ | $C_2H_5NH_2$ | 0.31 |
| $Zr(O_3P(CH_2)_{10}PO_3)_{\frac{1}{2}}(O_3POH)_1$ | $(C_8H_{17})_3N$ | 0.00 |

EXAMPLE XXVI

Zirconium bis(2-cyanoethylphosphate) was prepared by slurrying 6.311 g of barium 2-cyanoethylphosphate in deionized water, acidifying with 2 ml of concentrated hydrochloric acid and mixing with 2.199 g of zirconyl chloride octahydrate.

A white precipitate formed, and the mixture (of about 100 ml total volume) was heated and maintained at about 90° C. over a weekend.

The solid was isolated by filtration and washed successively with deionized water, acetone and ethyl ether, then dried at about 50° C. for about one hour. The yield was 2.886 g.

Elemental analysis of the solid yielded the following: 17.12% C and 2.89% H. The X-ray powder diffraction pattern for this solid indicates a semicrystalline state, with very low reflection intensities.

Other metal$^{+4}$ ions which are analogous to $Zr^{+4}$ in the process to make phosphate and phosphonate analogs, are metals with approximately the same ionic radius as $Zr^{+4}$ (0.8 Å), for example,

| | | | | | | | |
|---|---|---|---|---|---|---|---|
| $Zr^{+4}$ | 0.80Å | $Te^{+4}$ | 0.81 | $Pr^{+4}$ | 0.94 | $Mn^{+4}$ | 0.5 |
| $W^{+4}$ | 0.66 | $Sn^{+4}$ | 0.71 | $Pb^{+4}$ | 0.92 | $Ir^{+4}$ | 0.66 |
| $U^{+4}$ | 0.89 | $Si^{+4}$ | 0.41 | $Os^{+4}$ | 0.67 | $Hf^{+4}$ | 0.81 |
| $Ti^{+4}$ | 0.68 | $Ru^{+4}$ | 0.65 | $Nb^{+4}$ | 0.67 | $Ge^{+4}$ | 0.53 |
| $Th^{+4}$ | 0.95 | $Pu^{+4}$ | 0.86 | $Mo^{+4}$ | 0.68 | $Ce^{+4}$ | 1.01 |

The thio analogs of the phosphonates and phosphates can also be made by this process. The larger, more readily redoxable elements can lead to semiconducting, photoactive supports. All of the above noted solid, layered compounds can be useful as a chromatographic solid phase, adsorbants ion-exchange and hosts or carriers for controlled release of active substances.

In the preparation of anchorable Layered Compounds, a general approach to zirconium phosphate and the other zirconium compositions described herein and in the applications incorporated herein involve the following concepts:

(1) Tetrahedral anions with 3-metal coordinating groups and one interlayer group desirable

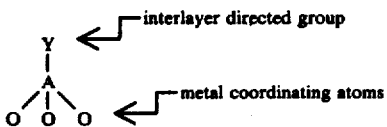

(2) Charge on anion should be $-1$, $-2$, $-3$ (charge on metal ion therefore should be $+2$, $+4$, $+6$ for M[$O_3AY]_2$ stoichiometry needed for sandwiching and bridging configuration)

(i) for $-1$ charge, conjugate acid of anion is

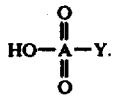

"A" can be S (or Se, Cr, Mo, W, etc., ($+6$ forming elements)

(ii) for $-2$ charge, conjugate acid of anion

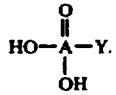

"A" can be P, As, Sb, V, Nb, Ta, etc., ($+5$ forming elements)

(iii) for $-3$ charge, conjugate acid of anion is

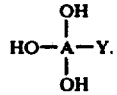

"A" can be Si, Ge, Ti, Zr, Sn, Pb ($+4$ forming elements).

Some exemplary salts which meet these criteria are listed below.

M[$O_3A$-Y]$_2$: Examples of compounds of structure which can form layered host structures analogous to zirconium phosphate and the phosphorus or arsenic containing compounds of the applications incorporated herein:

| | |
|---|---|
| (1) $[O_3A-Y]^{-1}$ | A = S, for example, Y = NH$_2$ (conjugate acid is sulfamic acid) M+ = Cu$^{+2}$, Zn$^{+2}$, Fe$^{+2}$, alkaline earths |
| 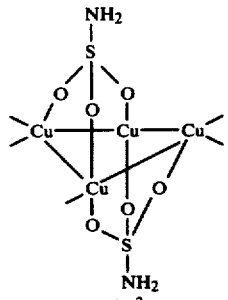 | |
| (2) $[O_3A-Y]^{-2}$ | Zirconium phosphate prototypes (A = P, As, Sb, etc.) |
| (3) $[O_3A-Y]^{-3}$ | A = Si, for example, Y = OCH$_2$CN M = Mo$^{+6}$ In all cases, metal ion is in octahedral sphere (could be trigonal prism) |
| 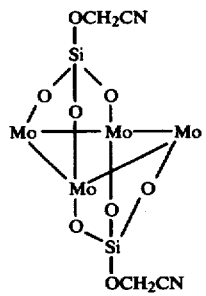 | |

Although the structure of these solid phases is polymeric in nature, it is convention in solid inorganic nomenclature to refer to them by their monomeric units.

What is claimed is:

1. Solid inorganic polymers derived from acyclic organo group-containing phosphorus or phosphoric acids, wherein three oxygens bonded to phosphorus are structurally linked to one or more tetravalent metals selected from the group consisting of titanium, zirconium, cerium, hafnium, lead, thorium and uranium, and wherein the molar ratio of phosphorus to tetravalent metal is about 2 to 1.

2. Solid inorganic polymers, as in claim 1, providing pendant organo groups, and which contain structural units of the formula

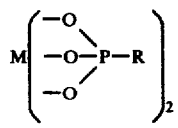

wherein R is an acyclic organo group, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

3. Solid inorganic polymers, as in claim 1, providing layer bridging organo groups, and which contain structural units of the formula

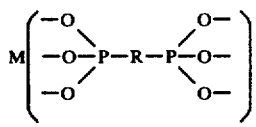

wherein R is an acyclic organo group which contains two or more carbon atoms, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

4. Solid inorganic polymers, as in claim 1, which are phosphonates, providing pendant organo groups, and which contain structural units of the formula

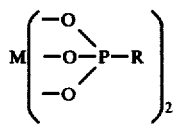

wherein R is an acyclic organo group which is bonded to phosphorus through carbon, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

5. Solid inorganic polymers, as in claim 4, in which R contains from 1 to about 20 carbon atoms.

6. Solid inorganic polymers, as in claim 1, which are phosphates, providing pendant organo groups, and which contain structural units of the formula

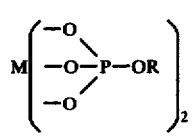

wherein R is an acyclic organo group which is bonded to phosphorus through an oxygen-carbon bond, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

7. Solid inorganic polymers, as in claim 6, in which R contains from 1 to about 20 carbon atoms.

8. The composition of claim 4, which is an inorganic polymer of zirconium bis(chloromethylphosphonate).

9. The composition of claim 4, which is an inorganic polymer of thorium bis(chloromethylphosphonate).

10. The composition of claim 4, which is an inorganic polymer of lead bis(chloromethylphosphonate).

11. The composition of claim 4, which is an inorganic polymer of titanium bis(chloromethylphosphonate).

12. The composition of claim 4, which is an inorganic polymer having the empirical formula $Zr(O_3PCH_2CH_2NH_3{}^+Cl^-)_2$.

13. The composition of claim 3, which is an inorganic polymer having the empirical formula $Zr(O_3PCH_2CH_2CH_2PO_3)$.

14. The composition of claim 4, which is an inorganic polymer of titanium bis(methylphosphonate).

15. The composition of claim 4, which is an inorganic polymer of thorium bis(methylphosphonate).

16. The composition of claim 4, which is an inorganic polymer of zirconium bis(methylphosphonate).

17. The composition of claim 4, which is an inorganic polymer of thorium bis(octadecylphosphonate).

18. The composition of claim 4, which is an inorganic polymer having the empirical formula $Zr(O_3PCH_2C_6H_5)_2$.

19. The composition of claim 4, which is an inorganic polymer having the empirical formula $Zr(O_3PCH_2CHCH_2)_2$.

20. The composition of claim 4, which is an inorganic polymer having the empirical formula $Zr[O_3PCH_2CH_2(NC_5H_5)^+Br^-]_2$.

21. The composition of claim 3, which is an inorganic polymer having the empirical formula $Zr[O_3P(CH_2)_{10}PO_3]$.

22. The composition of claim 3, which is an inorganic polymer having the empirical formula $Zr(O_3PCH_2CH_2PO_3)$.

23. The composition of claim 4, which is an inorganic polymer of zirconium bis(2-chloroethylphosphonate).

24. The composition of claim 4, which is an inorganic polymer of zirconium bis(2-bromoethylphosphonate).

25. Solid inorganic phosphorus-containing polymers providing pendant organo groups, and which contain structural units of the formula $$M(O_3PR)_2 \text{ or } M(O_3POR)_2$$

wherein R is an acyclic organo group containing three or more carbon atoms, three oxygens bonded to phosphorus are structurally linked to one or more tetravalent metals, M, selected from the group consisting of titanium, cerium, hafnium, lead, thorium and uranium, and wherein the molar ratio of phosphorus to tetravalent metal is about 2 to 1.

* * * * *